United States Patent [19]
Naka

[11] Patent Number: 5,910,663
[45] Date of Patent: Jun. 8, 1999

[54] OPTICAL SYSTEM AND LIGHT EMITTING DIODE HAVING A LIGHT DIVIDING SURFACE PORTION

[75] Inventor: Michio Naka, Kyoto, Japan

[73] Assignee: Kyoto Daiichi Kagaku Co., Ltd., Kyoto-fu, Japan

[21] Appl. No.: 08/916,174

[22] Filed: Aug. 21, 1997

[30] Foreign Application Priority Data

Aug. 23, 1996 [JP] Japan .................................. 8-222194

[51] Int. Cl.[6] ...................................................... H01L 27/15
[52] U.S. Cl. ...................... 257/81; 257/82; 257/98; 257/99; 257/100
[58] Field of Search ................................ 257/80, 81, 82, 257/84, 99, 100, 98

[56] References Cited

U.S. PATENT DOCUMENTS 4,733,094  3/1988  Carpentier et al. .

5,304,819  4/1994  Torazawa et al. ..................... 257/82

FOREIGN PATENT DOCUMENTS 0 472963   3/1992   European Pat. Off. .
0 623922  11/1994   European Pat. Off. .
61-219186  9/1986   Japan .

*Primary Examiner*—Minh Loan Tran
*Attorney, Agent, or Firm*—Birch, Stewart, Kolasch & Birch, LLP

[57] ABSTRACT

An optical analyzer includes a light emitting diode (LED). The LED has a body pervious to light and a PN junction semiconductor. The body has a surface portion where a primary light emitted from semiconductor is divided into a first light and a second light. The first light is reflected at a sample and then received by a first detector, while the second light is detected by a second detector. An optical property of the sample is determined by the use of outputs of the first and second detectors.

18 Claims, 4 Drawing Sheets

OPTICAL SYSTEM AND LIGHT EMITTING DIODE HAVING A LIGHT DIVIDING SURFACE PORTION

BACKGROUND OF THE INVENTION

The invention relates to a light emitting diode for use with an optical apparatus. Also, the invention relates to an optical apparatus for determining an optical property of a sample.

Conventionally, in the field of laboratory examination, there has been used a variety of optical apparatuses or analyzers which comprises a light source for emitting light onto a sample to be analyzed, and a light detector for receiving the light reflected from (or transmitted through) the sample in order to determine the reflectance (or transmittancy) of the sample. Further, in a small sized analyzer, a light emitting diode having a PN junction semiconductor has been preferably employed for the light source.

FIG. 6 illustrates an optical system which has been used for such an analyzer. The analyzer includes a light source or light emitting diode (LED) 10 for emitting a light Q1. The emitted light Q1 is illuminated on a test sample (not shown) on a plate 11. Then, a reflected light Q2 from the sample is detected by an optical sensor 12. The sensor 12 transmits a signal having a voltage corresponding to an intensity of the reflected light to obtain the reflectance of the sample on the plate 11.

Disadvantageously and undeniably, a luminous efficiency of the LED tends to vary depending upon an environmental temperature and electric current (voltage) to be applied and to decrease in proportion to its service time. Also, the change of luminous efficiency will adversely provide the measured result with error. Therefore, it is important to determine the intensity of light emitted from the LED at measurement and, if necessary, the resultant measurement should be corrected based upon the change of light efficiency.

One method for determining the change of light intensity of the emitted light, which is shown in FIG. 6, is to dispose a beam splitter 13 or a half-mirror across the light Q1 so that the light Q1 is divided into a measuring beam Q1' for illumination of the sample and a monitoring beam Q3 for detecting the light intensity of the light Q1 by the use of an optical sensor 14. Another method, which is shown in FIG. 7, is to dispose an optical sensor 15 beside LED 10 so that a feeble light Q3' emitted laterally from the light source 16 is detected, thereby determining the intensity of the light Q1.

The first method, however, renders the analyzing system more complicated and larger in size because of the additional arrangement of the beam splitter 13 or half mirror between the LED 10 and the test sample.

The second method has another drawback that the intensity of feeble light emitted laterally does not directly reflect the intensity of light Q1. Specifically, FIG. 8 is a graph showing a direction dependency of the light intensity of the LED. In this graph, a curve G1 illustrates a direction dependency in each direction against the light intensity of light Q1 having the maximum light intensity, in which the intensity of light emitted in the lateral direction spaced at 90 degrees from the upright direction is only about 30% of that of the upright direction. Further, another curve G2 also illustrates a direction dependency when the light intensity in the upright direction is reduced to 50% by decreasing the voltage (current) applied to LED in which the light intensity of lateral direction is only about 10%, not 30%, of that of the upright direction in curve G1.

More disadvantageously, the light intensity varies with the environmental temperature as well as the emitting direction. This is illustrated in a three dimensional graph of FIG. 9 in which X, Y and Z axes represent an angle of each direction from the upright direction when the upright direction is zero degree, environmental temperature (from 5 to 50 degrees centigrade) and light intensity in each direction, respectively. In this graph, the light intensity in each direction is standardized at 5 degrees centigrade. This shows that the intensity of light changes with the environmental temperature, but the increasing rate in one direction differs from that of another direction. Namely, with the increase of the environmental temperature, the ratio of light intensity between the monitoring light Q3' and the primary light Q1 varies depending upon the emitting angle.

It is believed that the direction dependency of the light intensity is caused by a variation of density of the current which flows in the light source, that may occur from differences of electric properties of assembled devices, connecting condition of electrodes of the light emitting diode, and the like.

Thus, the light intensity of the primary light Q1 emitted in the normal direction could not be determined precisely by the detection of the monitoring light Q3' emitted laterally, inhibiting the precise measurement of the optical property of the sample.

Accordingly, it is an object of the invention to provide a light emitting diode which is preferably used in the optical apparatus.

It is another object of the invention to provide an optical apparatus for use in an optical analyzer.

It is still another object of the invention to provide an optical apparatus capable of measuring an optical property such as reflectance or transmittancy of the test sample with a great precision.

SUMMARY OF THE INVENTION

A light emitting diode of the invention comprises a body made of resin pervious to light and a light source having a semiconductor mounted in the body for emitting a primary light. The body has a surface portion where the primary light emitted from the light source is divided into a first light for an optical analysis and a second light for monitoring an intensity of the primary light.

Preferably, the surface portion of the body has small convex and concave portions for dividing the primary light into the first and second lights.

More preferably, the surface portion is slanted with respect to the primary light so that the first light is a light which is reflected at the surface portion and the second light is a light which is scattered at the surface portion.

The surface potion may be a V-shaped recess having first and second surfaces that intersect at a certain angle so that the primary light is divided at an intersection of the first and second surfaces into the first light projected and then reflected on the first surface and the second light projected and then reflected on the second surface.

An optical apparatus of the invention comprises a light emitting diode. The light emitting diode includes a body made of resin which is pervious to light and a light source having a semiconductor mounted in the body for emitting a primary light. The body has a surface portion where the primary light emitted from the light source is divided into a first light which is intended to be illuminated on a sample and a second light for monitoring an intensity of the primary light. The apparatus further comprises a first detector for detecting the first light from the sample, a second detector for detecting the second light and means for determining an optical property of the sample from outputs of the first and second detectors.

The light emitting diode and the first and second detectors may be integrally molded in a body of resin. In this instance, preferably the resin of the molded body is impervious to light and the molded body includes a first passage for guiding the first light toward the sample, a second passage for guiding a light reflected from the sample toward the first detector and a third passage for guiding the second light toward the second detector.

According to the invention, the primary light emitted from the light source is divided at the surface portion of the body of the light emitting diode into first and second lights. Subsequently, the first light is reflected at or transmitted through the sample and then detected by the first detector while the second light is detected by the second detector. The output of the first detector is used for determining the optical property of the sample. The output of the second detector, on the other hand, is used for determining the light intensity of the primary light, thereby correcting the resultant optical property. Therefore, the optical property of the sample can be determined with great precision even when the intensity of the light emitted from the light source has varied due to the changes of voltage or current applied with the light source and/or the environmental temperature.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

Corresponding reference characters indicate corresponding parts throughout the several views of the drawings.

DETAILED DESCRIPTION OF THE PREFERRED EMBODIMENT

Figure 1:
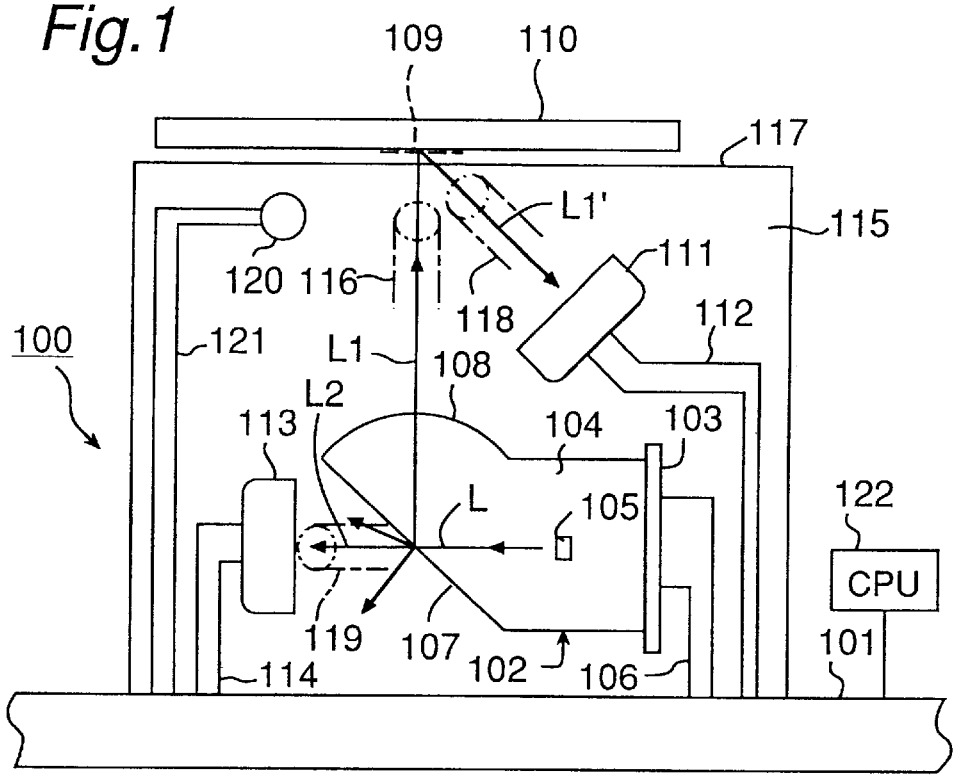
FIG. 1 is a cross-sectional side elevational view of an optical analyzer of the invention.
Figure 2:
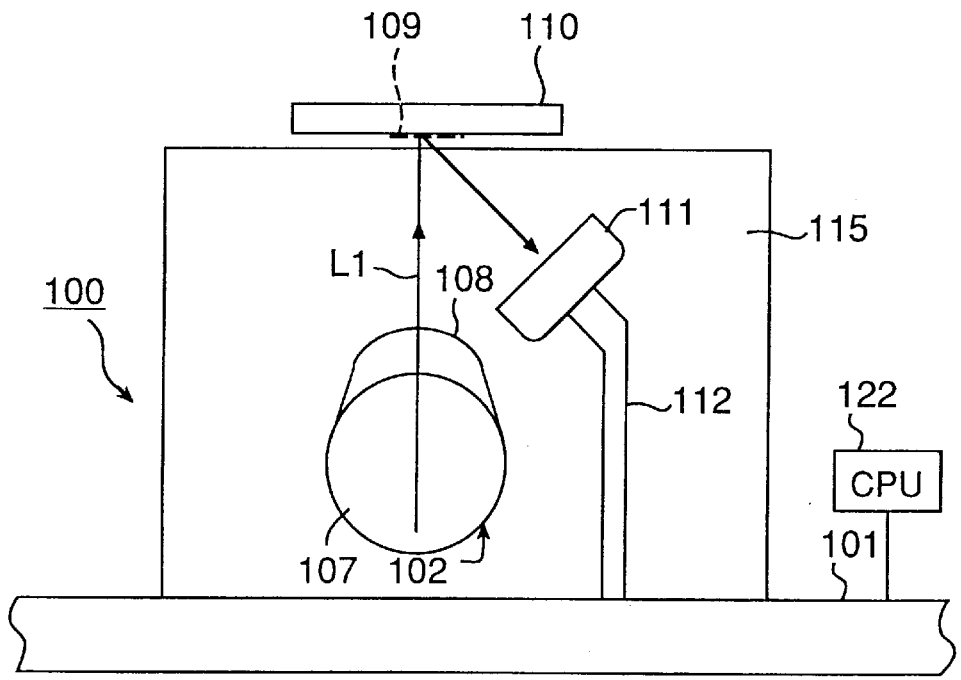
FIG. 2 is another cross-sectional side elevational view of the optical analyzer of FIG. 1.

With reference to the drawings, in particular to FIG. 1, an optical analyzer of the invention generally indicated by reference numeral 100 includes a printed circuit board 101 having an electric circuit (not shown) on both or either side thereof. A light emitting diode (LED) generally indicated by reference numeral 102 has a base 103, body 104 made of resin (e.g., epoxy resin) pervious to light, PN junction semiconductor 105 integrally molded in the body 104 and capable of emitting light when it is applied with voltage, and a pair of terminals 106 electrically communicating the semiconductor 105 with the circuit on the printed circuit board 101. The semiconductor 105 is so directed that a primary light L having the maximum light intensity is emitted vertical to and away from base 103.

The body 104 generally in the form of a solid cylinder is secured at its one end to the base 103. The other end of body 104 remote from the base 103 is formed with a surface 107 which is slanted at about 45 degrees against the longitudinal axis of the body 104. Also, the body 104 is formed at its peripheral portion adjacent the slanted surface 107 with a domed surface portion or convex lens 108, so that most of the primary light L emitted from the semiconductor 105 is reflected at the slanted surface 107 and then transmitted substantially along a central axis of the convex lens 108 toward a sample 109 (e.g., urine, blood, or chemical compound) retained on a sample retaining plate 110 (e.g., PET (polyethylene terephthalate) plate) to be releasably disposed above the circuit board 101. The body 104 is typically formed by molding and therefore undoubtedly the slanted surface 107 has small or microscopic convex and concave portions therein rather than being a perfect mirror, so that the primary light L emitted from the semiconductor 105 in part scatters out of the slanted surface 107. The LED 102 thus constructed is so arranged that the reflected primary light L1 travels in a direction away from the circuit board 101 toward the sample 109.

A first optical sensor 111 having a pair of terminals 112 is disposed above the LED 102 so that it can detect a part of light L1' of the primary light L which would be reflected at the sample 109. Preferably, the first optical sensor 111 is so oriented that it can receive the reflected light L1' traveling in a direction which intersects with the primary light L1 advancing to the sample 109 at an angle of 45 degrees. Also, a second optical sensor 113 having a pair of terminals 114 is disposed to oppose the slanted surface 107 of LED 102 so that it can detect the scattered light L2 at the slanted surface 107. This arrangement ensures that a ratio of light intensity between the primary light and the scattered light is independent of driving condition of LED 102 and therefore the light intensity detected by the optical sensor 111 can be corrected using the detected light intensity of the scattered light. The optical sensors 111 and 113 are commercially available under the trade designation PIN photodiode (SPS-503A1) from SANYO ELECTRIC CO., Ltd. Also, the terminals 112 and 114 are secured on the printed circuit board 101 and electrically communicated with the circuit on the board 101.

Preferably, LED 102 and optical sensors 111 and 113 are integrally molded in a molded body 115 on the circuit board 101 with a resin, such as ABS, which is impervious to light. The molded body 115 includes therein a first passage 116 which extends from the convex lens 108 to one surface 117, such as the top surface, facing the sample retaining plate 110, and a second passage 118 which extends from the first optical sensor 111 to the top surface 117 so that the primary light L1 from the semiconductor 105 can travel through the first passage 116 to illuminate the sample 109 on the sample retaining plate 110 and then the reflected light L1' travels to the first optical sensor 111. The molded body 115 also includes a third passage 119 which extends from the slanted surface 107 to the second optical sensor 113 so that the scattered light L2 of the primary light can reach the second optical sensor 113.

Preferably, the passages 117, 118 and 119 are formed in the molded body 115 by arranging tubes corresponding to respective passages in a mold prior to the molding of body 115.

Preferably, openings of the first and second passages 116 and 118, confronting the sample 109, are covered with a transparent plate (not shown) to prevent foreign matter from entering into the passages 116 and 118.

More preferably, a thermal sensor 120 is integrally mounted in the molded body 115 for detecting a temperature. The thermal sensor 120 includes a pair of terminals 121 which are electrically connected with the circuit on the board 101. It is to be understood that the thermal sensor 120 may be disposed outside the molded body 115.

Also, mounted on the circuit board 101 is a central processing unit (CPU) 122 which is electrically connected with the LED 102, the first and second optical sensors 111 and 113 and the thermal sensor 120.

Having described the general construction of the optical analyzer 100, its operation will now be described. Firstly, a reference plate (not shown) which retains thereon a reference sample having a known reflectance of, for example, 50%, is so positioned that the reference sample confronts the openings of the passages 116 and 118. The CPU 122 instructs the LED 102 to energize the semiconductor 105 for emitting light. The primary light L emitted from the semiconductor 105 travels toward the slanted surface 107 where the major part thereof is reflected. The reflected primary light L1 further travels through the convex lens 108 and first the passage 116 to reach the sample 109 on the sample retaining plate 110 where it is reflected again. Part of the second reflected primary light L1' travels into second passage 118 to the first optical sensor 111 which detects the intensity of the second reflected primary light L1'. The optical first sensor 111 outputs a signal corresponding to the detected light intensity to the CPU 122. The primary light L from the semiconductor 105 scatters at the slanted surface 107 due to the existence of the microscopic convex and concave portions. The scattered light L2 travels through the third passage 119 to reach the second optical sensor 113. The second optical sensor 113 outputs a signal corresponding to the intensity of the detected scattered light L2 to the CPU 122. In addition, the thermal sensor 120 outputs a signal corresponding to the temperature of the molded body 115 to the CPU 122. With the signals from the optical sensors 111 and 113, the CPU 122 corrects data stored therein so that the calculated reflectance of the reference plate will be 50%.

Secondly, the reference plate is replaced by the sample retaining plate 110 retaining a test sample 109 so that the test sample 109 confronts the openings of the passages 116 and 118. The CPU 122 performs the same process to determine the reflectance of the sample 109 from the light intensity detected by the first optical sensor 111 using the light intensity detected by the second optical sensor 113 according to the following equation:

$$R_{SAM} = R_{REF} \cdot [V_{SAM}(1) \cdot V_{REF}(2)] / [V_{SAM}(2) \cdot V_{REF}(1)]$$

where $R_{SAM}$: Reflectance of test sample $V_{REF}(1)$: Output voltage of first optical sensor for reference sample $V_{REF}(2)$: Output voltage of second optical sensor for reference sample $V_{SAM}(1)$: Output voltage of first optical sensor for test sample $V_{SAM}(2)$: Output voltage of second optical sensor for test sample Specifically, assume that the reference plate has a reflectance $R_{REF}$ of 50% and output voltages $V_{REF}(1)$ and $V_{REF}(2)$ of the first and second optical sensors 111 and 113 are 44 milli-volts and of 4.2 milli-volts, respectively. Also assume that, for the test sample on the sample retaining plate replaced by the reference plate, outputs voltages $V_{SAM}(1)$ and $V_{SAM}(2)$ of the first and second optical sensors 111 and 113 are 12 milli-volts and 4.2 milli-volts. In this instance, the reflectance of the sample can be obtained as follows:

$$R_{SAM} = R_{REF} \cdot V_{SAM}(1) / V_{REF}(1)$$

$$= 50 \cdot 12 / 44$$

$$= 13.6\%$$

Alternately, if the output voltage $V_{SAM}(2)$ is decreased to 4.0 milli-volts, the reflectance of the sample will be obtained as follows:

$$R_{SAM} = R_{REF} \cdot [V_{SAM}(1) \cdot V_{REF}(2)] / [V_{SAM}(2) \cdot V_{REF}(1)]$$

$$= 50 \cdot [12 \cdot 4.2] / [44 \cdot 4.0]$$

$$= 14.3\%$$

Figure 3:
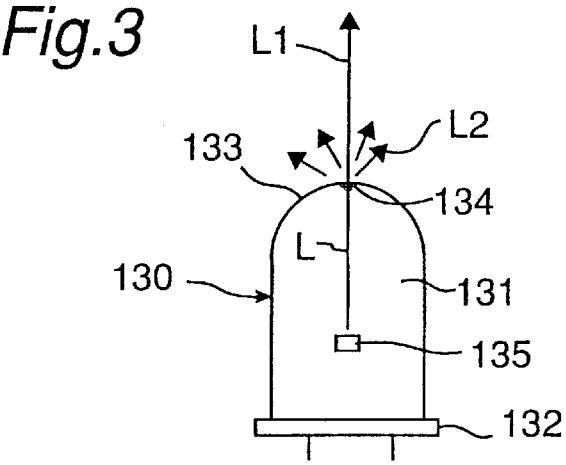
FIG. 3 is a side elevational view of a light emitting diode of another embodiment according to the invention.

The invention is not limited to the embodiment described and it may be modified in different manners. For example, as shown in FIG. 3, an LED 130 may have a conventional configuration. In this instance, the body 131 of the LED 130 is formed at its distal end away from the base 132 with a domed surface 133. Also, a central portion 134 of the domed surface 133 is formed with small or microscopic convex and concave portions by a suitable manner such as sandblasting. Instead, the convex and concave portions may be formed at molding of the body 131 by providing corresponding convex and concave portions on an inner surface of the mold. With this LED 130, the primary light L emitted from the semiconductor 135 scatters in part at the central portion 134. Therefore, by detecting the scattered light L2 using the optical sensor, the light intensity of the primary light can be corrected.

Typically, the molded surface includes microscopic convex and concave potions. Therefore, it is not necessary to form such small convex and concave portions by the above described techniques. In this event, a feeble scattering light is generated when the primary light transmits the surface of the LED body. Therefore, by detecting the feeble scattering light by the optical sensor, the light intensity of the primary light can be corrected.

Figure 4:
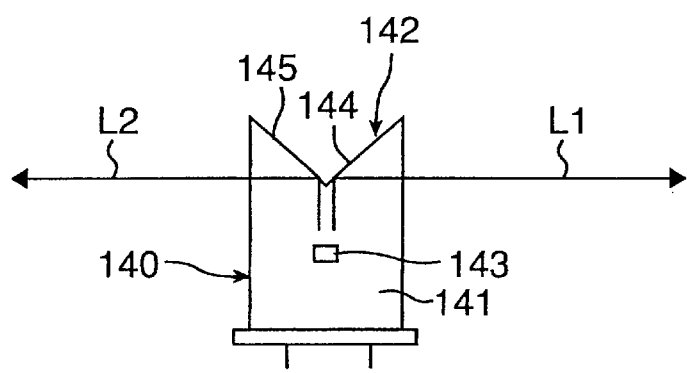
FIG. 4 is a side elevational view of the light emitting diode of another embodiment according to the invention.

FIG. 4 shows another embodiment of the invention. In this embodiment, the body 141 of an LED 140 has a V-shaped recess 142 with its bottom portion confronting the semiconductor 143. Preferably, two surfaces 144 and 145 of the V-shaped recess 142 are spaced apart from each other at 90 degrees. In this event, the primary light emitted from the semiconductor 143 is illuminated at the bottom portion of the V-shaped recess 142 where it is divided into two, one light L1 reflected at the surface 144 and then being transmitted in one direction for illumination of test sample and the other light reflected at the surface 145 and then transmitted in the opposite direction for monitoring.

Figure 5:
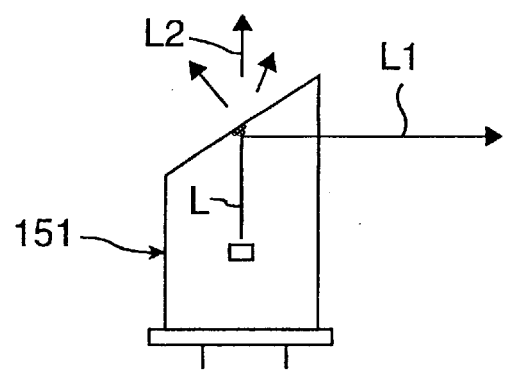
FIG. 5 is a side elevational view of the light emitting diode of another embodiment according to the invention.
Figure 6:
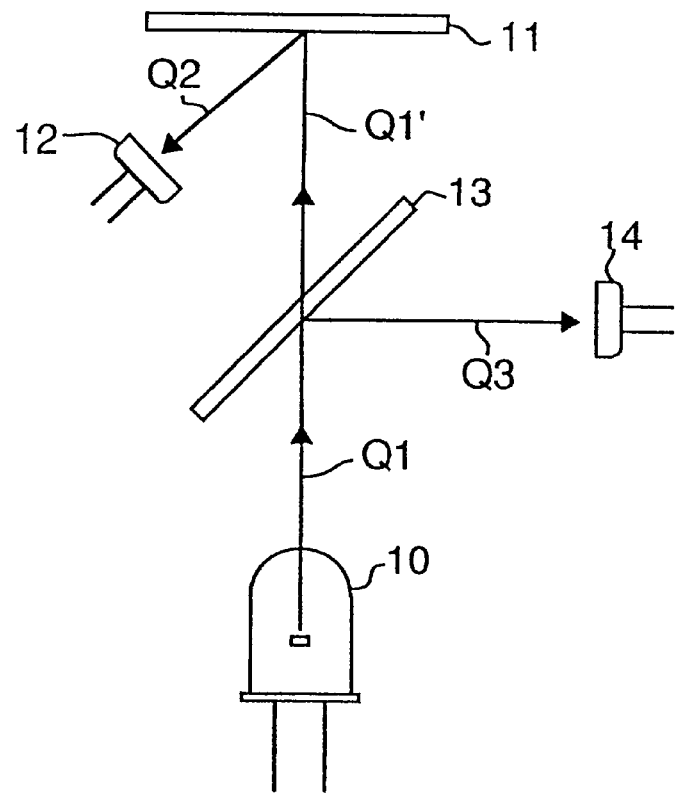
FIG. 6 is a side elevational view of a conventional optical analyzer.
Figure 7:
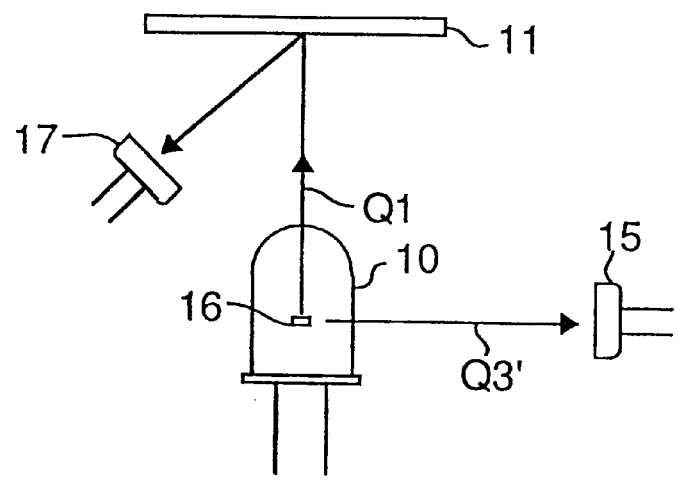
FIG. 7 is a side elevational view of another conventional optical analyzer.
Figure 8:
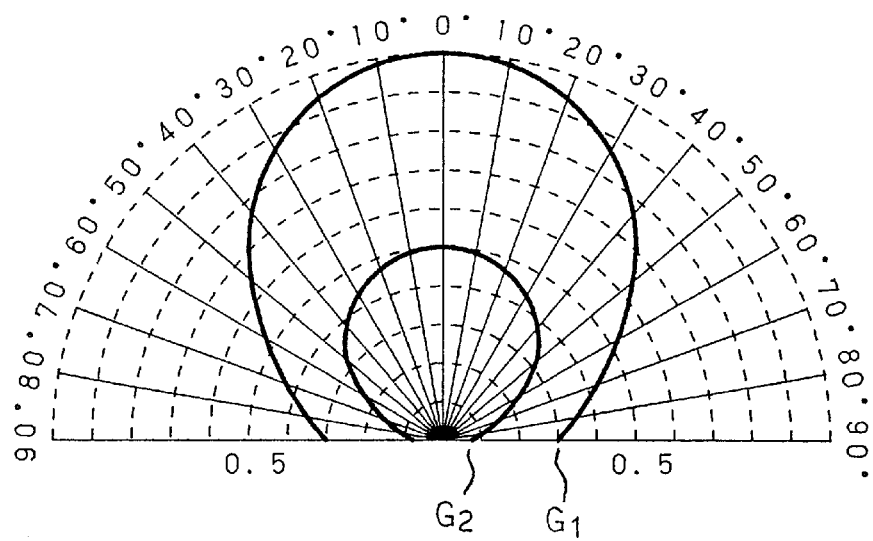
FIG. 8 is a graph showing a directional dependency of intensity of the light emitted from the light emitting diode.
Figure 9:
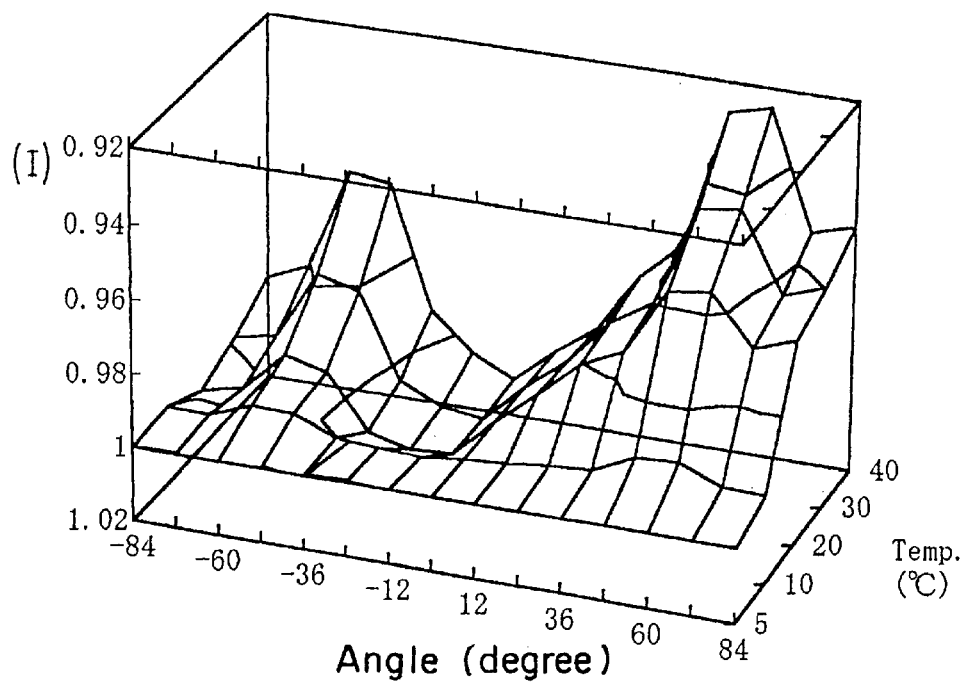
FIG. 9 is a three dimensional graph showing a temperature dependency of intensity of the light emitted from the light emitting diode.

FIG. 5 shows still another embodiment of an LED body 151 in which the domed surface or convex lens is eliminated therefrom.

Although the optical analyzer is designed to determine the reflectance of the sample, it may be modified to determine a transmittancy of light.

In view of the above, it will be seen that the several objects of the invention are achieved and other advantageous results are attained.

As various changes could be made in the above constructions without departing from the scope of the invention, it is intended that all matter contained in the above description or shown in the accompanying drawings shall be interpreted as illustrative and not in a limiting sense.

What is claimed is:

1. A light emitting diode for use in an optical analyzer, comprising:

a body made of resin which is pervious to light; and a light source having a semiconductor mounted in said body for emitting light, a portion of said light having a first intensity defining a primary light;

said body having a surface portion for dividing said primary light of said first intensity into a first light for an optical analysis and a second light for monitoring an intensity of said primary light.

2. A light emitting diode claimed in claim 1, wherein said surface portion of said body has small convex and concave portions for dividing said primary light into said first and second lights.

3. The light emitting diode claimed in claim 1, wherein said first intensity is a substantially maximum intensity of said light.

4. A light emitting diode for use in an optical analyzer, comprising:

a body made of resin which is pervious to light; and a light source having a semiconductor mounted in said body for emitting a primary light;

wherein said body has a surface portion where said primary light emitted from said light source is divided into a first light for an optical analysis and a second light for monitoring an intensity of said primary light, wherein said surface portion is slanted with respect to said primary light so that said first light is a light which is reflected at said surface portion and said second light is a light which is scattered at said surface portion.

5. A light emitting diode for use in an optical analyzer, comprising:

a body made of resin which is pervious to light; and a light source having a semiconductor mounted in said body for emitting a primary light;

wherein said body has a surface portion where said primary light emitted from said light source is divided into a first light for an optical analysis and a second light for monitoring an intensity of said primary light, wherein said surface portion is a V-shaped recess having first and second surfaces that intersect at a certain angle so that said primary light is divided at an intersection of said first and second surfaces into said first light projected and then reflected on said first surface and said second light projected and then reflected on said second surface.

6. An optical system for use in an optical analyzer, comprising:

a light emitting diode which includes a body made of resin which is pervious to light; and a light source having a semiconductor mounted in said body for emitting light, a portion of said light having a first intensity defining a primary light;

said body having a surface portion for dividing said primary light of said first intensity into a first light which is to be illuminated on a sample and a second light for monitoring an intensity of said primary light;

a first detector for detecting said first light reflected at or transmitted through said sample;

a second detector for detecting said second light; and means for determining an optical property of said sample from outputs of said first and second detectors.

7. An optical system claimed in claim 6, wherein said surface portion of said body has small convex and concave portions for dividing said primary light into said first and second lights.

8. An optical system claimed in claim 6, wherein said light emitting diode and said first and second detectors are integrally molded in a body of resin.

9. An optical system claimed in claim 8, wherein said resin of said molded body is impervious to light and said molded body includes a first passage for guiding said first light toward said sample, second passage for guiding a light reflected from said sample toward said first detector and a third passage for guiding said second light toward said second detector.

10. The optical system claimed in claim 9, wherein said body further includes a thermometer.

11. The optical system claimed in claim 9, further comprising a plate on which said sample is retained.

12. The optical system claimed in claim 8, wherein said body further includes a thermometer.

13. The optical system claimed in claim 8, further comprising a plate on which said sample is retained.

14. An optical system claimed in claim 6, wherein said body further includes a thermometer.

15. An optical system claimed in claim 6, further comprises a plate on which said sample is retained.

16. The optical system claimed in claim 6, wherein said first intensity is a substantially maximum intensity of said light.

17. An optical system for use in an optical analyzer, comprising:

a light emitting diode which includes
      a body made of resin which is pervious to light; and
      a light source having a semiconductor mounted in said body for emitting a primary light;
      wherein said body has a surface portion where said primary light emitted from said light source is divided into a first light which is intended to be illuminated on a sample and a second light for monitoring an intensity of said primary light;

a first detector for detecting said first light reflected at or transmitted through said sample, a second detector for detecting said second light; and means for determining an optical property of said sample from outputs of said first and second detectors, wherein said surface portion is slanted with respect to said primary light that said first light is a light which is reflected at said surface portion and said second light is a light which is scattered at said surface portion.

18. An optical system for use in an optical analyzer, comprising:
- a light emitting diode which includes
  - a body made of resin which is pervious to light; and
  - a light source having a semiconductor mounted in said body for emitting a primary light;
  - wherein said body has a surface portion where said primary light emitted from said light source is divided into a first light which is intended to be illuminated on a sample and a second light for monitoring an intensity of said primary light;
- a first detector for detecting said first light reflected at or transmitted through said sample;
- a second detector for detecting said second light; and
- means for determining an optical property of said sample from outputs of said first and second detectors,
- wherein said surface portion is a V-shaped recess shaving first and second surfaces that intersect at a certain angle so that said primary light is divided at an intersection of said first and second surfaces into said first light projected and then reflected on said first surface and said second light projected and then reflected on said second surface.

* * * * *